US012661618B2

(12) United States Patent (10) Patent No.: US 12,661,618 B2
Beck et al. (45) Date of Patent: Jun. 23, 2026

(54) FILTRATION DEVICE

(71) Applicant: GAMBRO LUNDIA AB, Lund (SE)

(72) Inventors: Christof Beck, Bitz (DE); Steffen Wagner, Messtetten (DE); Bernd Hertzler, Balingen (DE); Rainer Blickle, Bitz (DE); Stefan Ermantraut, Balingen (DE)

(73) Assignee: GAMBRO LUNDIA AB, Lund (SE)

( * ) Notice: Subject to any disclaimer, the term of this patent is extended or adjusted under 35 U.S.C. 154(b) by 367 days.

(21) Appl. No.: 16/604,288

(22) PCT Filed: Apr. 11, 2018

(86) PCT No.: PCT/EP2018/059317
§ 371 (c)(1),
(2) Date: Oct. 10, 2019

(87) PCT Pub. No.: WO2018/189254
PCT Pub. Date: Oct. 18, 2018

(65) Prior Publication Data
US 2020/0047128 A1 Feb. 13, 2020

(30) Foreign Application Priority Data

Apr. 12, 2017 (EP) ..................................... 17166295

(51) Int. Cl.
*B01D 63/02* (2006.01)
*A61M 1/16* (2006.01)
(Continued)

(52) U.S. Cl.
CPC ......... *B01D 63/024* (2013.01); *A61M 1/1672* (2014.02); *B01D 63/021* (2013.01);
(Continued)

(58) Field of Classification Search
CPC .. B01D 63/024; B01D 63/021; B01D 63/022; B01D 63/0223; B01D 63/033;
(Continued)

(56) References Cited

U.S. PATENT DOCUMENTS

| | | | | |
|---|---|---|---|---|
| 3,505,686 A | * | 4/1970 | Bodell | B01D 63/02 |
| | | | | 623/66.1 |
| 4,547,289 A | * | 10/1985 | Okano | B01D 65/102 |
| | | | | 210/321.89 |

(Continued)

FOREIGN PATENT DOCUMENTS

| | | | | |
|---|---|---|---|---|
| DE | 3513789 A1 | * | 10/1986 | B01D 63/024 |
| EP | 0105858 A2 | * | 4/1984 | B29C 66/542 |

(Continued)

OTHER PUBLICATIONS

PCT Search Report and Written Opinion prepared for PCT/EP2018/059317, completed Jun. 19, 2018.

*Primary Examiner* — Akash K Varma
(74) *Attorney, Agent, or Firm* — Barnes & Thornburg LLP

(57) ABSTRACT

The present disclosure relates to a filtration device comprising a plurality of hollow fiber membranes. In particular, a filtration device comprising a plurality of microporous hollow fiber membranes having a large inner diameter and a thin wall is provided. The filtration device can be used for sterile dead-end filtration of liquids destined for infusion into a patient. Processes for production of the filtration device are also provided.

10 Claims, 4 Drawing Sheets

(51) Int. Cl.

| | |
|---|---|
| *B01D 65/00* | (2006.01) |
| *B01D 69/08* | (2006.01) |
| *B01D 71/48* | (2006.01) |
| *B29C 65/00* | (2006.01) |
| *B29C 65/16* | (2006.01) |
| *C02F 1/44* | (2023.01) |
| *B29L 31/14* | (2006.01) |

(52) U.S. Cl.

CPC ......... *B01D 63/022* (2013.01); *B01D 65/003* (2013.01); *B01D 69/081* (2013.01); *B01D 71/48* (2013.01); *B29C 65/1616* (2013.01); *B29C 65/1677* (2013.01); *B29C 66/1222* (2013.01); *B29C 66/73921* (2013.01); *C02F 1/44* (2013.01); *A61M 2202/0468* (2013.01); *B01D 2313/041* (2022.08); *B01D 2313/13* (2013.01); *B01D 2313/21* (2013.01); *B01D 2315/08* (2013.01); *B29L 2031/14* (2013.01)

(58) Field of Classification Search

CPC ...... B01D 63/061; B01D 63/02; B01D 63/06; B01D 63/0241; B01D 63/00; B01D 65/003; B01D 65/00; B01D 69/081; B01D 69/02; B01D 69/08; B01D 69/00; B01D 71/48; B01D 71/62; B01D 71/68; B01D 2313/041; B01D 2313/13; B01D 2313/21; B01D 2313/04; B01D 2313/206; B01D 2313/2061; B01D 2315/08; B01D 2323/58; B01D 2325/0283; B01D 2325/02831; B01D 2325/16; C02F 1/44; A61M 1/1672; A61M 1/16; A61M 2202/0468; A61M 5/165; B29C 65/1612; B29C 65/1616; B29C 65/1677; B29C 65/1635; B29C 65/16; B29C 65/00; B29C 66/1222; B29C 66/73921; B29C 66/1142; B29C 66/1224; B29C 66/5344; B29C 66/5414; B29C 66/5416; B29C 66/71; B29C 66/543; B29L 2031/14; B29L 31/14; B29K 2023/06

USPC ........................................................ 210/650

See application file for complete search history.

(56) References Cited

U.S. PATENT DOCUMENTS

| | | | | |
|---|---|---|---|---|
| 5,202,023 A * | 4/1993 | Trimmer | ............... | B01D 53/22 |
| | | | | 210/321.89 |
| 2007/0163942 A1* | 7/2007 | Tanaka | ................. | B01D 63/043 |
| | | | | 210/321.89 |
| 2012/0325746 A1* | 12/2012 | Tamai | .................... | B01D 63/02 |
| | | | | 29/592 |
| 2013/0075321 A1* | 3/2013 | Hobbs | .................... | B01D 71/36 |
| | | | | 210/321.78 |

FOREIGN PATENT DOCUMENTS

| | | | | |
|---|---|---|---|---|
| EP | 2883597 | | 6/2015 | |
| EP | 2883597 A1 * | 6/2015 | .......... | B01D 63/021 |
| KR | 20140066471 A * | 6/2014 | | |
| WO | WO-2012043672 A1 * | 4/2012 | ............ | B01D 63/02 |

* cited by examiner

10

A-A

FILTRATION DEVICE

CROSS-REFERENCE TO RELATED APPLICATIONS

This application is the U.S. national phase of PCT/EP2018/059317, filed on Apr. 11, 2018, which claims the benefit of European Patent Application Serial Number 17166295.0, filed on Apr. 12, 2017, the entire disclosures of both of which are incorporated herein by reference.

TECHNICAL FIELD

The present disclosure relates to a filtration device comprising a plurality of hollow fiber membranes, a process for its production, and its use for the dead-end filtration of infusion liquids.

DESCRIPTION OF THE RELATED ART

Liquids destined to be infused into a patient's body, in particular into the bloodstream of a patient, have to be free of pyrogens and particulate matter. To protect the patient, infusion solutions therefore typically are passed through a filter device installed in the infusion line before they enter the patient's body. Commercially available devices generally comprise a microporous flat sheet membrane. Filter devices comprising hollow fiber membranes instead of flat sheet membranes also have been proposed.

U.S. Pat. No. 4,267,053 A discloses an inline intravenous final filter unit comprising a casing having an inlet cap at its one end and an outlet cap at the other end. At least one porous hollow fiber having a porosity rating of 0.1 to 5 $\mu$m is arranged within the casing parallel to the longitudinal direction thereof. The hollow fiber is closed at its one end opposed to the inlet cap, and open at the other end thereof opposed to the outlet cap. The hollow fiber further is tightly fixed at the outer peripheral portion of its open end to the inner wall of the casing by a securing member; and the ratio of the total effective filtration area of the hollow fiber to the capacity of the casing is at least about 4:1. The hollow fiber membranes have an outside diameter of up to 3 mm and an inner diameter of at least 0.5 mm.

In the working examples of U.S. Pat. No. 4,267,053 A, a filter device is disclosed comprising 16 porous hollow fibers having 0.5 mm inside diameter and 1.4 mm outside diameter, 60 mm in length and 0.32 $\mu$m in porosity rating. The fibers are accommodated in a hollow cylindrical casing 8 mm in inside diameter, 10 mm in outside diameter and 80 mm in length and tightly secured to the inner wall of the casing by securing member made of a silicone-type adhesive material. The porous hollow fibers are made from cellulose diacetate, and the casing, inlet cap and outlet cap from polyethylene. The filter unit has a filtration area, A, of 35.2 cm$^2$ and an A/V ratio of 5.61. The hollow fiber membranes used have a ratio of inside diameter/wall thickness of 0.5 mm/0.45 mm=1.1. The liquid to be filtered permeates from the outside of the hollow fibers into the lumen. Flow rates of less than 35 ml/cm$^2$*hr are reported.

The device of U.S. Pat. No. 4,267,053 A is suitable for filtering infusion solutions at a rate of some 500 ml per hour. By expanding the filtration area, this value might be increased to a certain extent. However, for filtering large volumes of liquid in a short time, a different kind of filtration device is required. It is an objective of the present disclosure to provide a filtration device capable of filtering large volumes of liquid in a short time.

SUMMARY

The present application provides a filtration device comprising a plurality of microporous hollow fiber membranes having a large inner diameter and a thin wall. The device can be used for sterile dead-end filtration of liquids destined for infusion into a patient.

DETAILED DESCRIPTION

Figure 1:
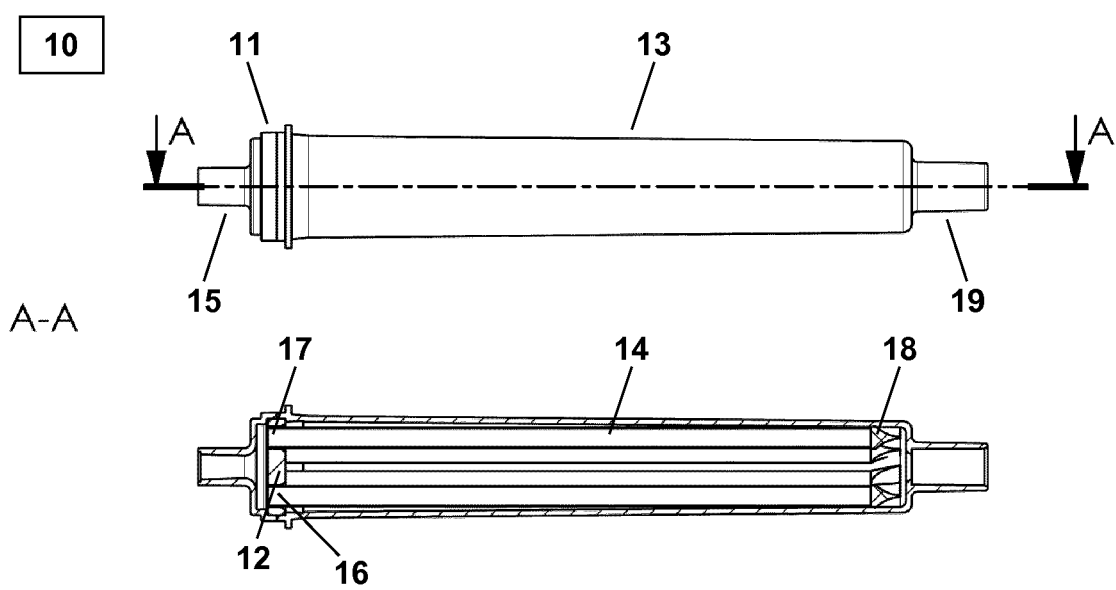
FIG. 1 is a side view and a cross-sectional view of an embodiment of the filtration device 10 of the present disclosure.

The present invention provides filtration devices comprising a plurality of semipermeable hollow fiber membranes.

The filtration device 10 of the present disclosure comprises a header section 11 having an inlet 15 for a liquid. In one embodiment, the header section 11 shows cylindrical symmetry, the axis running through the inlet 15. The header section 11 covers a first face of a disk 12 having a plurality of bores 16 and holding a plurality of hollow fiber membranes 14 which protrude from a second face of the disk 12, opposite to the first face covered by the header section 11. In one embodiment, a circumferential ledge 21 is present on the inside wall of the header section 11; and disk 12 is seated on the ledge 21. In another embodiment, a flange 23 is provided on the mouth of header section 11.

The filtration device 10 of the present disclosure comprises a disk 12 having a plurality of bores 16. The number of bores 16 is not particularly limited. The disk 12 generally comprises three or more bores 16, for instance, 4 to 36 bores, e.g., 6 to 19 bores, or 5 to 8 bores. In one embodiment, the disk 12 features 5 bores. In another embodiment, the disk 12 features 6 bores. In still another embodiment, the disk 12 features 7 bores. In one embodiment, the thickness of the disk is in the range of from 1 to 10 mm, for instance, 2 to 5 mm.

In one embodiment, the bores 16 of the disk 12 form a regular pattern. This offers the advantage that the liquid to be filtered is more evenly distributed between the individual bores 16 and the corresponding semipermeable hollow fiber membranes 14 than with a random arrangement obtained by potting the ends of the hollow fiber membranes 14 with a reactive polymer, as described in U.S. Pat. No. 4,267,053 A. A more uniform liquid flow results in enhanced performance of the filtration device 10. In one embodiment, the bores 16 are arranged in a circular pattern, i.e., their centers are located on the circumference of a circle. In another embodiment, the centers of the bores 16 are located on the circumferences of two coaxial circles. In still another embodiment, the centers of the bores 16 are located on the circumferences of three coaxial circles. In a further embodiment, one bore 16 is located in the center of the disk 12 and the centers of the other bores 16 are located on the circumference(s) of one or more coaxial circles. In another embodiment, the bores 16 form a trigonal or hexagonal mesh; or a rectangular or quadratic mesh.

Each bore 16 holds a first end 17 of a semipermeable hollow fiber membrane 14. The diameter of the bore 16 is a little larger than the outer diameter of the semipermeable hollow fiber membrane 14, in order to facilitate introduction of the first end 17 of the fiber into the bore 16. In one embodiment, the difference is in the range of from 0.05 to 0.3 mm. The semipermeable hollow fiber membrane 14 protrudes from the disk 12 and is sealed at its second end 18. In one embodiment, the lip of the first end 17 of the semipermeable hollow fiber membrane 14 is level with one face of the disk 12; and the semipermeable hollow fiber membrane 14 protrudes from the opposite face of the disk 12.

The first end 17 of the semipermeable hollow fiber membrane 14 is fixed to the wall of the bore 16. In one embodiment, the first end 17 of the semipermeable hollow fiber membrane 14 is welded or fused to the wall of the bore 16. In another embodiment, the first end 17 of the semipermeable hollow fiber membrane is glued to the wall of the bore 16 using a suitable adhesive, for instance, an epoxy resin or a polyurethane adhesive.

The second end 18 of the semipermeable hollow fiber membrane 14 is sealed, so that any liquid entering the first end 17 of the semipermeable hollow fiber membrane 14 can only leave the fiber through the membrane wall, being filtered in the process. In one embodiment, the seal is generated by melting the second end 18 of the semipermeable hollow fiber membrane 14. In another embodiment, the seal is generated by crimping or clamping the second end of the semipermeable hollow fiber membrane 14. In still another embodiment, the seal is generated by sealing the second end 18 of the semipermeable hollow fiber membrane 14 with a sealing material, e.g., an adhesive or a reactive resin.

In one embodiment, a circumferential ridge 26 is present on the peripheral surface of disk 12. The height of the ridge 26 is equal to or less than the wall thickness of header section 11 and tubular section 13. The outer diameter of disk 12 including the ridge matches the outer diameter of header section 11 and tubular section 13, while the outer diameter of disk 12 adjacent to the ridge 26 matches the inner diameter of header section 11 and tubular section 13, respectively. When the filtration device 10 is assembled, the ridge 26 is held between the lips of header section 11 and tubular section 13, respectively. Ridge 26 is joined to the lips of header section 11 and tubular section 13, respectively, thus sealing filtration device 10.

In another embodiment, disk 12 features a collar 24 on its peripheral surface. The outer diameter of collar 24 matches the outer diameter of corresponding flanges 23 and 25 provided on the header section 11 and the tubular section 13, respectively. The outer diameter of disk 12 adjacent to collar 24 matches the inner diameter of header section 11 and tubular section 13, respectively. When the filtration device 10 is assembled, collar 24 is held between flanges 23 and 25.

Flange 23 is joined to one face of collar 24; and flange 25 is joined to the other face of collar 24, thus sealing filtration device 10.

In one embodiment, the outer diameter of the disk 12 at its maximal extension matches an outer diameter of the header section 11 and the tubular section 13. In another embodiment, the outer diameter of disk 12 at its maximal extension matches an inner diameter of the header section 11 and the tubular section 13. In one embodiment, disk 12 is seated in a circumferential recess in the inner wall of filtration device 10. In one embodiment, the circumferential recess spans the interface of header section 11 and tubular section 13. In another embodiment, the circumferential recess spans the mouths of both header section 11 and tubular section 13.

The filtration device 10 of the present disclosure further comprises a tubular section 13 having an outlet 19 for a liquid. In one embodiment, the tubular section 13 shows cylindrical symmetry, the axis running through the outlet 19. The tubular section 13 encloses the plurality of semipermeable hollow fiber membranes 14 protruding from the disk 12, i.e., it provides a housing for the fibers. Therefore, the length of the tubular section 13 has to be larger than the length of the semipermeable hollow fiber membranes 14 protruding from the disk 12, so that the semipermeable hollow fiber membranes 14 fit into the tubular section 13. Generally, the length of the tubular section 13 will exceed the length of the semipermeable hollow fiber membranes 14 protruding from the disk 12, so that there is a gap between the second end 18 of the semipermeable hollow fiber membranes 14 and the outlet 19. In one embodiment, the width of the gap is in the range of from 0.1 to 10 mm.

In one embodiment, a circumferential ledge 20 is present on the inside wall of the tubular section 13. Disk 12 is seated on ledge 20. In one embodiment, circumferential ledges 20 and 21 are present on the inside wall of the tubular section 13 and the header section 11, respectively. Disk 12 is held by the circumferential ledges 20 and 21, which together form a circumferential recess in the inner wall of filtration device 10.

In one embodiment of the filter device, the header section 11, the disk 12 and the tubular section 13 each comprise a thermoplastic polymer.

Suitable materials for the header section 11 and the tubular section 13 include polyesters, polycarbonates, acrylonitrile-butadiene-styrene copolymers (ABS), styreneacrylonitrile copolymers (SAN), styrene-methyl methacrylate copolymers (SMMA), styrene-butadiene-copolymers (SBC), polyvinylchlorides (PVC), polyolefins, and copolymers and blends thereof. In one embodiment of the invention, the materials of the header section 11 and the tubular section 13 comprise polyesters, for instance, polycarbonates, polyethylene terephthalates (PET), or glycol-modified polyethylene terephthalates (PETG). In a particular embodiment of the invention, the polyester is a glycol-modified polyethylene terephthalate (PETG).

In one embodiment, the header section 11 and the tubular section 13 are comprised of materials substantially transparent to IR light, i.e., showing low absorption in the wavelength range of from 700 to 1,500 nm.

Suitable materials for the disk 12 include polyolefins; polyesters like polycarbonates; acrylic polymers like MMA or SMMA; polyamides like nylon; SAN; SBA; and ABS. In one embodiment of the invention, the disk 12 comprises glycol-modified polyethylene terephthalate (PETG). Disk 12 does not need to be transparent to IR light. For some embodiments of the filtration device 10 of the present disclosure, it is even essential that the disk 12 absorbs IR radiation.

In one embodiment, the disk 12 comprises an IR absorber, i.e., a material which absorbs infrared light. The IR absorber is dispersed in the polymer matrix of the disk 12. Suitable IR absorbers include carbon black; inorganic pigments like Lazerflair® pigments, copper phosphates or indium tin oxide (ITO); and organic pigments which have a high absorption in the wavelength range of from 700 to 1500 nm, for instance, phthalocyanines, naphthalocyanines, metal complexes of azo dyes, anthraquinones, squaric acid derivatives, immonium dyes, perylenes, quaterylenes and polymethins. Of these, phthalocyanines and naphthalocyanines are particularly suitable. Phthalocyanines and Naphthalocyanines having bulky side groups are preferred, due to their improved solubility in thermoplastic polymers. In a particular embodiment, the IR-absorptive material comprises a phthalocyanine. In another particular embodiment, the IR-absorptive material comprises carbon black.

The amount of IR absorber contained in the thermoplastic polymer of disk 12 is not particularly restricted as long as the desired absorption of laser radiation is ensured. In one embodiment, the thermoplastic polymer contains from 0.1 to 10 wt.-%, e.g., from 1 to 5 wt.-% of IR absorber, relative to the total weight of the thermoplastic polymer. Mixtures of different infrared absorbers can also be used. By mixing IR absorbers having absorption maxima at different wavelengths, the skilled person can optimize the absorption in the wavelength region of the laser used for the welding step. The IR absorber is compounded into the thermoplastic polymer of disk 12 by processes customary in the art. In a particular embodiment, disk 12 is comprised of PETG comprising 3 to 5 wt.-% carbon black.

In one embodiment, disk 12 is cut or punched out from a sheet of the IR absorber-containing thermoplastic polymer having the desired thickness. In another embodiment of the invention, disk 12 is produced from the IR absorber-containing thermoplastic polymer by way of injection molding.

In one embodiment of the filtration device 10, the semipermeable hollow fiber membranes 14 have an inner diameter of from 2.8 to 4.0 mm, for instance, from 3.0 to 3.7 mm, or from 3.1 to 3.5 mm; and a wall thickness of from 100 to 500 μm, for instance, from 180 to 320 μm. The outer diameter of the semipermeable hollow fiber membranes 14 is larger than 3 mm. The ratio of inner diameter to wall thickness of the membranes is larger than 10, or even larger than 15. Membranes having a large ratio of inner diameter to wall thickness, i.e. thin-walled membranes, are more flexible and easily deformable. These membranes are less prone to form kinks on bending than thick-walled membranes. The ends of the thin-walled hollow fibers also can readily be closed by crimping to produce dead-end filter elements.

In one embodiment of the filtration device 10, the semipermeable hollow fiber membranes 14 have a mean flow pore size, determined by capillary flow porometry, in the range of from 0.2 to 0.5 μm.

Capillary flow porometry is a liquid extrusion technique in which the flow rates through wet and dry membranes at differential gas pressure are measured. Before measurement, the membrane is immersed in a low surface tension liquid (e.g., a perfluoroether commercially available under the trade name Porofil®) to ensure that all pores including the small ones are filled with the wetting liquid. By measuring the pressure at which the liquid is pressed out of the pores their corresponding diameter can be calculated using the Laplace equation. With this method, the pore size distribution of those pores that are active in the mass transport is determined. Dead-end and isolated pores are omitted. The hollow fiber membranes are measured inside-out.

$$\text{Laplace equation: } Dp = 4\gamma \cos \theta / \Delta P$$

Dp=diameter of pores [m]

γ=surface tension [N/m]; for Porofil® 0.016 [N/m]

ΔP=pressure [Pa]

Cos θ=contact angle; for complete wetting cos θ=1

In one embodiment, the semipermeable hollow fiber membranes 14 comprise polyethersulfone (PESU) and polyvinylpyrrolidone (PVP). In one embodiment, the semipermeable hollow fiber membranes 14 additionally comprise a polymer bearing cationic charges. Examples of suitable polymers bearing cationic charges include polyethyleneimines, modified polyethyleneimines, and modified polyphenyleneoxides. Semipermeable hollow fiber membranes 14 comprising a polymer bearing cationic charges show increased retention of endotoxins.

The overall effective surface area of the plurality of semipermeable hollow fiber membranes 14 generally is larger than 5 cm$^2$. The effective surface area is the portion of the surface area of the semipermeable hollow fiber membranes 14 available for the filtration of liquid; i.e., the portion that is not covered by the walls of the bores 16 or sealed, like the second ends 18 of the semipermeable hollow fiber membranes 14. In one embodiment, the overall effective surface area of the plurality of semipermeable hollow fiber membranes 14 is in the range of from 10 cm$^2$ to 250 cm$^2$, e.g., from 20 to 100 cm$^2$, or from 30 to 60 cm$^2$.

The present disclosure also provides a process for operating the filtration device 10 of the present disclosure. The process comprises introducing a liquid through the inlet 15 of the filtration device 10 via bores 16 of disk 12 into the lumen of the plurality of semipermeable hollow fiber membranes 14; filtering the liquid through the walls of the plurality of semipermeable hollow fiber membranes 14; and removing the filtered liquid from the filtration device 10 through the outlet 19.

The filtration device 10 of the present disclosure is designed and configured for inside-out filtration, i.e., the liquid to be filtered is introduced through inlet 15 into the lumen of the semipermeable hollow fiber membranes 14, permeates through the membrane wall into the interior space of tubular section 13, and leaves the filtration device 10 through outlet 19. This allows for operating the filtration device 10 at pressures exceeding atmospheric pressure. In one embodiment, the filtration device 10 is operated at a pressure in the range of from 0.5 to 4 bar(g), for instance, 1.0 to 3.5 bar(g), or 1.5 to 2.5 bar(g). The filtration device 10 of the present disclosure achieves maximal flow rates, measured with water at 20° C. at 1.5 bar(g), of from 10 to 25 ml/cm$^2$*min, i.e., 600 to 1,500 ml/cm$^2$*hr.

In comparison, the device of U.S. Pat. No. 4,267,053 A achieves a maximal flow rate of 33.5 ml/cm$^2$*hr, or 0.56 ml/cm$^2$*min. Using a device of the present invention having an effective surface area of 30 cm$^2$, 500 ml of liquid can be filtered in about one minute; while it would require about one hour to do it with the device of U.S. Pat. No. 4,267,053 A.

In one embodiment of the filtration device 10 of the present disclosure, the header section 11 and the tubular section 13 are bonded to the disk 12. In one embodiment, bonding is achieved using a suitable adhesive, for instance, an epoxy resin or a polyurethane adhesive. In a particular embodiment, bonding is achieved using a UV-curable adhesive. In another embodiment, bonding is achieved using a thermosetting adhesive.

In one embodiment of the filtration device 10, the header section 11 and the tubular section 13 are fused or welded to the disk 12. In another embodiment of the filtration device 10, the header section 11 is fused or welded to the tubular section 13. Welding can be performed using customary techniques. Examples include friction welding, spin welding, ultrasonic welding, high frequency welding, radiant heat welding, mirror welding, and laser welding. Welding processes which do not generate particles are preferred. In a particular embodiment, laser welding is used to weld the header section 11 and the tubular section 13 of the filtration device 10 to the disk 12.

The present disclosure also provides a process for the production of the filter device 10. A disk 12 of a thermoplastic polymer comprising an IR-absorptive material is provided between the tubular section 13 and the header section 11. The disk 12 allows for laser-welding the header section 11 and the tubular section 13 to the disk 12, laser-welded joints being formed in the process.

In one embodiment, the present disclosure provides a process for producing a filter device 10 which comprises providing a header section 11 and a tubular section 13. Both sections comprise a thermoplastic polymer.

The process also comprises providing a disk 12 of a thermoplastic polymer comprising an IR-absorptive material. The disk 12 features a plurality of bores 16. Each bore 16 holds a first end 17 of a semipermeable hollow fiber membrane 14 which protrudes from the disk 12. The semipermeable hollow fiber membrane 14 is sealed at its second end 18.

In one embodiment of the process, the disk 12 holding a plurality of semipermeable hollow fiber membranes 14 is assembled in a preceding procedure. Semipermeable hollow fiber membranes 14 having the desired length are provided, and one end 18 of each fiber 14 is sealed, e.g., by heat sealing or heat crimping. The open end 17 of a semipermeable hollow fiber membrane 14 is introduced into a bore 16 of a disk 12 having a plurality of bores 16; and the fiber end 17 is fixed to the wall of the bore 16. In one embodiment of the process, the end 17 of the semipermeable hollow fiber membrane is fused or welded to the wall of the bore 16. In another embodiment, the end 17 of the semipermeable hollow fiber membrane is glued to the wall of the bore 16 using a suitable adhesive, for instance, an epoxy resin or a polyurethane adhesive. All bores 16 of the disk 12 are subsequently or simultaneously equipped with fibers in this way.

The process further comprises assembling the header section 11, the disk 12 holding the plurality of semipermeable hollow fiber membranes 14, and the tubular section 13. The three parts are combined in such a manner that the lip of the header section 11 and the lip of the tubular section 13 contact the disk 12. Header section 11 covers the bores 16 of the disk 12; and tubular section 13 encloses the plurality of semipermeable hollow fiber membranes 14 protruding from the disk 12.

In one embodiment of the process, the lip of the header section 11 and the lip of the tubular section 13 contact disk 12 on opposite faces of disk 12, or on opposite faces of a ridge 26 or a collar 24 located on the peripheral surface of disk 12.

In another embodiment, the inside of the lip of the header section 11 and the lip of the tubular section 13 contact the peripheral surface of disk 12, and the lip of the header section 11 and the lip of the tubular section contact each other. The outer diameter of disk 12 matches the inner diameter of the header section 11 and the tubular section 13, so that the peripheral surface of disk 12 touches the insides of both the header section 11 and the tubular section 13.

Subsequently to the assembly of the parts, the header section 11 is joined to the disk 12; and the disk 12 is joined to the tubular section 13 to produce the finished filter device 10. In one embodiment, header section 11 additionally is joined to tubular section 13. In one embodiment, joining is achieved by irradiation with laser light having a wavelength in the range of from 800 nm to 1090 nm.

In one embodiment of the joining process, irradiation with laser light is performed by at least one laser beam moving along a perimeter of the lip of the header section 11 and the tubular section 13, respectively. In another embodiment of the process, the whole perimeter of the lip of the tubular section 13 and the header section 11, respectively, is irradiated with laser light simultaneously using ring optics. In still another embodiment, the perimeters of the lip of the header section 11 and the tubular section 13 are irradiated with laser light simultaneously. The laser beam is absorbed by the disk 12 of thermoplastic polymer comprising an IR-absorptive material. The heat generated by the laser melts the thermoplastic polymer and creates a permanent weld, i.e., a laser-welded joint.

Examples of suitable lasers for the laser-welding step include semiconductor diode lasers having wavelengths in the range of 800 nm to 980 nm; and solid state lasers (e.g., fiber lasers or Nd:YAG lasers) having wavelengths in the range of from 1060 to 1090 nm. Depending on the materials and the desired welding speed, optical power levels of the laser range from 1 W to 200 W, e.g., from 20 to 100 W, for instance, 30 to 80 W.

In one embodiment of the process, the diameter of the focal spot of the laser beam is in the range of from 0.5 mm to 2 mm, for instance 0.8 mm to 1.5 mm.

In one embodiment of the process, the parts are pressed together during the joining step while the laser generates the weld seam. Generally, a force in the range of from 100 to 1,500 N is used to press the individual parts together. Depending on the diameter of the filter device 10 and the area the force is applied to, this translates to pressures in the range of from 1 to 5 $N/mm^2$.

The filtration device 10 of the present disclosure will typically be sterilized before it is used in a clinical setting. One suitable method is sterilization with ethylene oxide (ETO). In another embodiment, the filtration device 10 is sterilized with gamma radiation. In a particular embodiment, radiation dose used is in the range of from 25 to 50 kGy, for instance, 25 kGy. In still another embodiment, the filtration device 10 is sterilized with steam at a temperature of at least 121° C. for at least 21 min.

The present disclosure also is directed to the use of the filtration device 10 in the dead-end filtration of liquids. In one embodiment, the filtration device 10 is used for sterile filtration of water or aqueous solutions, e.g. drugs, dialysis liquids, or nutrient solutions, or other liquids destined for infusion into a patient. The filter device 10 retains particles, bacteria, and endotoxins that may be present in the liquid. The filtered liquid is pyrogen-free and may directly be injected into a patient.

Exemplary embodiments of the filtration device 10 of the present disclosure are shown in the accompanying figures and described below. It will be understood that the features mentioned above and those described hereinafter can be used not only in the combination specified but also in other combinations or on their own, without departing from the scope of the present invention.

FIG. 1 shows a side view and a cross-sectional view of an embodiment of a filtration device 10 of the present disclosure. The side view of filtration device 10 illustrates header section 11 with inlet 15 and tubular section 13 with outlet 19 together forming the outer shell of the filtration device 10. The cross-sectional view shows disk 12 holding a plurality of semipermeable hollow fiber membranes 14 arranged within the filtration device 10. Disk 12 comprises a plurality of bores 16. Each bore 16 holds the first end 17 of a semipermeable hollow fiber membrane 14. The wall of semipermeable hollow fiber membrane 14 is attached to the wall of the bore 16 at the first end 17. The second end 18 of semipermeable hollow fiber membrane 14 is sealed.

Figure 2:
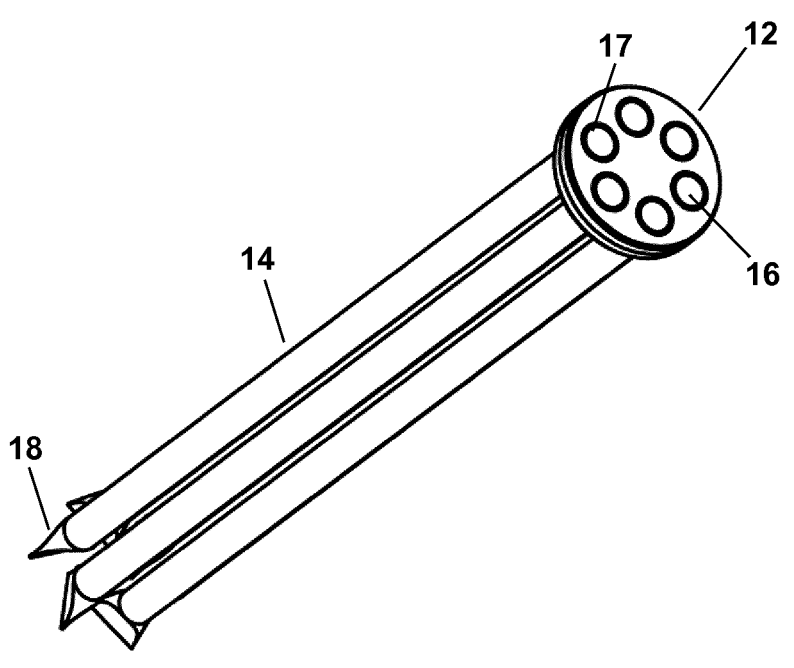
FIG. 2 is a perspective view of an embodiment of a disk 12 holding a plurality of semipermeable hollow fiber membranes 14.

FIG. 2 shows a perspective view of a disk 12 comprising a plurality of bores 16. Each bore 16 holds the first end 17 of a semipermeable hollow fiber membrane 14. The wall of semipermeable hollow fiber membrane 14 is attached to the wall of the bore 16 at the first end 17. The second end 18 of the semipermeable hollow fiber membrane 14 is sealed. The figure shows an embodiment wherein the second ends 18 of semipermeable hollow fiber membranes 14 have been sealed by crimping.

Figure 3:
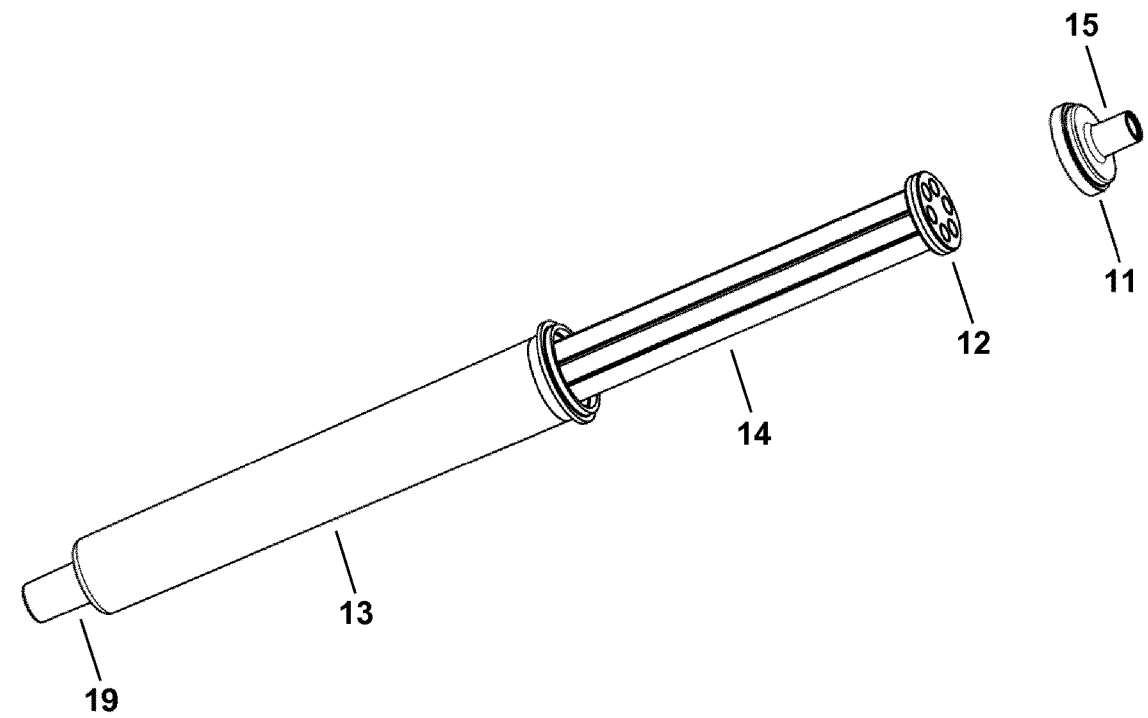
FIG. 3 is an exploded view of an embodiment of the filtration device 10 of the present disclosure.

FIG. 3 shows an exploded view of an embodiment of a filtration device 10. Disk 12 with a plurality of semipermeable hollow fiber membranes 14 attached thereto is arranged within tubular section 13, tubular section 13 providing a housing for the semipermeable hollow fiber membranes 14. Header section 11 covers disk 12 and seals the mouth of tubular section 13.

Figure 4:
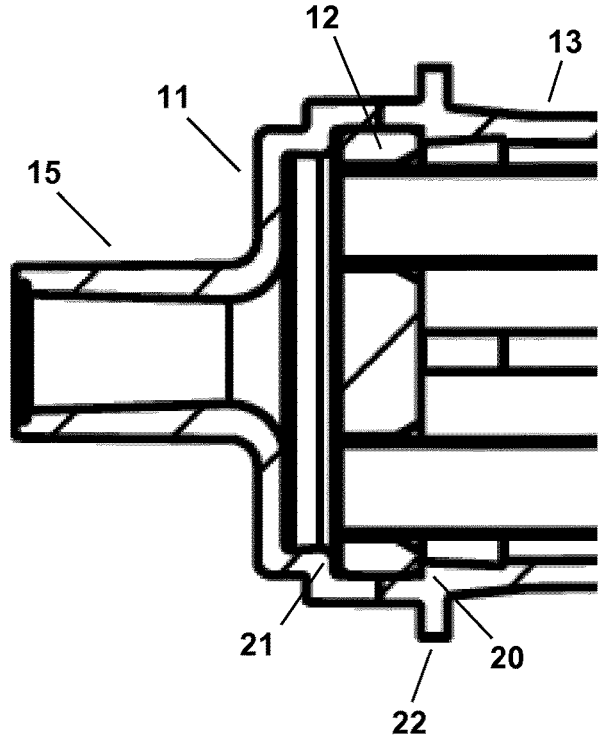
FIG. 4 is a detail of a cross-sectional view of the filtration device 10 shown in FIG. 1.

FIG. 4 shows a detail of the cross-sectional view of FIG. 1. Circumferential ledges 20 and 21 are present on the inside wall of the tubular section 13 and the header section 11, respectively. Disk 12 is held by the circumferential ledges 20 and 21, which together form a circumferential recess in the inner wall of filtration device 10. A collar 22 is present on the outside surface of tubular section 13. Collar 22 is an optional feature of the device. It is provided as an anchor for fastening the filtration device 10 in a holder.

Figure 5:
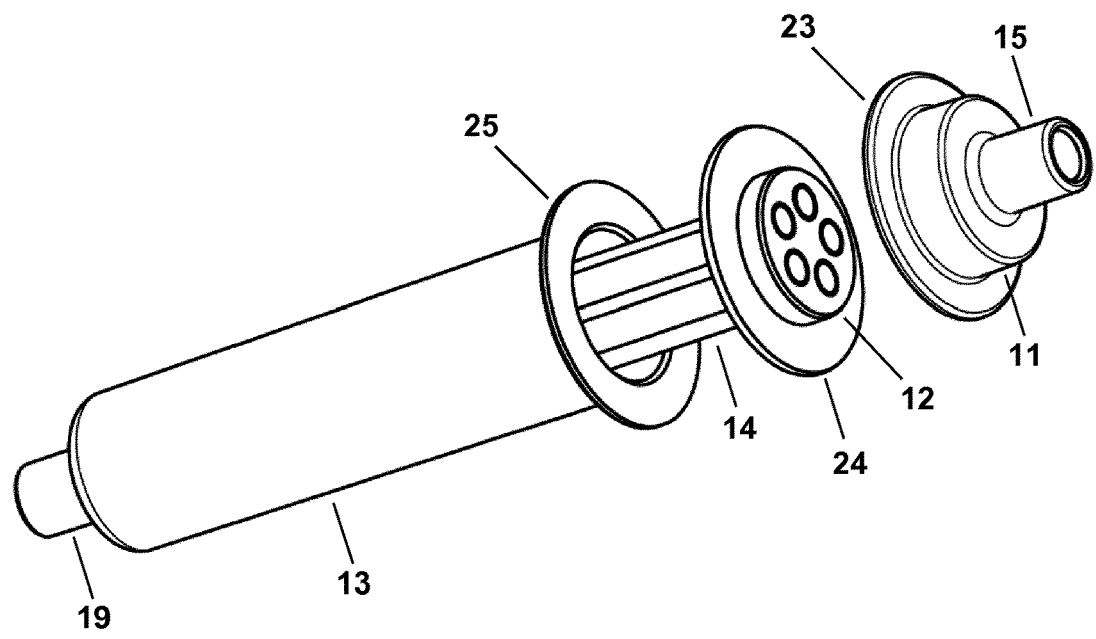
FIG. 5 is an exploded view of another embodiment of the filtration device 10 of the present disclosure.

FIG. 5 shows an exploded view of another embodiment of a filtration device 10. Disk 12 with a plurality of semipermeable hollow fiber membranes 14 attached thereto is arranged within tubular section 13, tubular section 13 providing a housing for the semipermeable hollow fiber membranes 14. Disk 12 features a collar 24 on its perimeter. A flange 23 is provided on the mouth of header section 11; and another flange 25 is provided on the mouth of tubular section 13. The outer diameter of collar 24 matches the outer diameter of flanges 23 and 25. Collar 24 is held between flanges 23 and 25 when the filtration device 10 is assembled. Flange 23 is joined to one face of collar 24; and flange 25 is joined to the other face of collar 24, thus sealing filtration device 10. Joining can be achieved by bonding the parts together using an adhesive; or by fusing or welding them. In one embodiment, disk 12 including collar 24 is comprised of an IR-absorbing material and flanges 23 and 25 are joined to collar 24 by laser welding.

Figure 6:
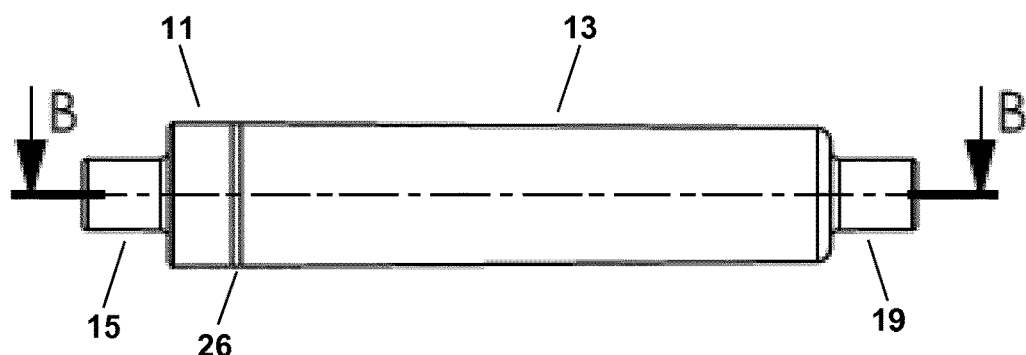
FIG. 6 is a side view and a cross-sectional view of still another embodiment of the filtration device 10 of the present disclosure.
Figure 6:
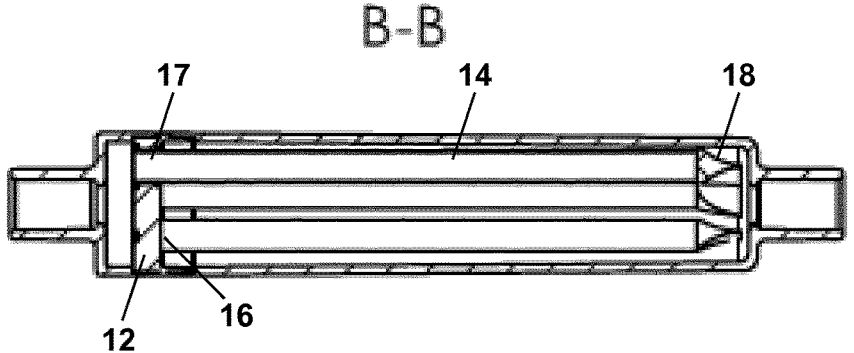

FIG. 6 shows a side view and a cross-sectional view of still another embodiment of a filtration device 10 of the present disclosure. The side view of filtration device 10 illustrates header section 11 with inlet 15; tubular section 13 with outlet 19; and disk 12 with ridge 26 together forming the outer shell of the filtration device 10. The cross-sectional view shows disk 12 holding a plurality of semipermeable hollow fiber membranes 14 arranged within the filtration device 10. Disk 12 comprises a plurality of bores 16. Each bore 16 holds the first end 17 of a semipermeable hollow fiber membrane 14. The wall of semipermeable hollow fiber membrane 14 is attached to the wall of the bore 16 at the first end 17. The second end 18 of semipermeable hollow fiber membrane 14 is sealed.

Figure 7:
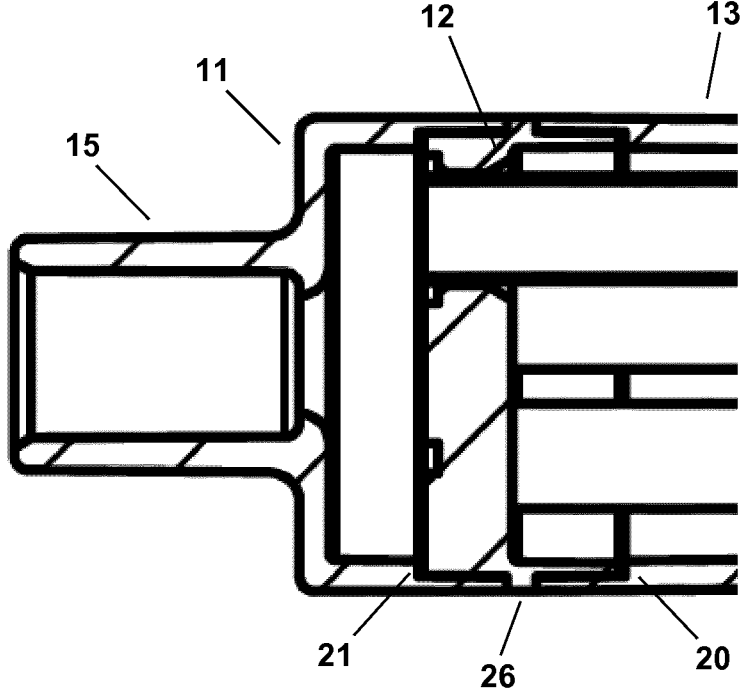
FIG. 7 is a detail of a cross-sectional view of the filtration device 10 shown in FIG. 6.

FIG. 7 shows a detail of the cross-sectional view of FIG. 6. A circumferential ridge 26 is present on the peripheral surface of disk 12. Ridge 26 is held between the lips of header section 11 and tubular section 13, respectively, when the filtration device 10 is assembled. Header section 11, tubular section 13, and ring 12 are joined at ridge 26, thus sealing filtration device 10. Joining can be achieved by bonding the parts together using an adhesive; or by fusing or welding them. In one embodiment, disk 12 including ridge 26 is comprised of an IR-absorbing material and tubular section 13 and header section 11 are joined to ridge 26 by laser welding.

LIST OF REFERENCE SIGNS 10 filtration device
11 header section
12 disk
13 tubular section
14 semipermeable hollow fiber membrane
15 liquid inlet
16 bore
17 first end of hollow fiber membrane
18 second end of hollow fiber membrane
19 liquid outlet
20 ledge
21 ledge
22 collar
23 flange
24 collar
25 flange
26 ridge

The invention claimed is:

1. A filtration device comprising:
a header section having an inlet for receiving an unfiltered liquid into the filtration device,
a disk having a plurality of bores formed therein, the plurality of bores being defined by one or more walls within the disk,
a plurality of semipermeable hollow fiber membranes, each semipermeable hollow fiber membrane having a first end and a second end, wherein the first end is welded to the one or more walls, wherein one or more semipermeable hollow fiber membranes is protruding from the disk, and wherein the second end is individually sealed by crimping and wherein the second end of each of the plurality of semipermeable hollow fiber membranes is not attached to any singular structure; and
a tubular section having an outlet for removing a filtered liquid from the filtration device;
wherein the header section covers a first face of the disk, wherein a lip of the header section contacts the disk and a lip of the tubular section contacts the disk, and wherein both the header section and the tubular section are welded to the disk; and
wherein the tubular section covers a second face of the disk opposite the first face, and wherein the tubular section encloses the plurality of semipermeable hollow fiber membranes;
wherein the header section, the disk, and the tubular section each comprise a thermoplastic polymer; and wherein the disk comprises an infrared absorptive (IR-absorptive) pigment selected from the group consisting of carbon black, IR-absorptive inorganic pigments, and IR-absorptive organic pigments.

2. The filtration device of claim 1, wherein the IR-absorptive pigment comprises a phthalocyanine.

3. The filtration device of claim 1, wherein the thermoplastic polymer is glycol-modified polyethylene terephthalates (PETG).

4. The filtration device of claim 1, wherein both the header section and the tubular section are bonded to the disk.

5. The filtration device of claim 1, wherein both the header section and the tubular section are welded to the disk.

6. The filtration device of claim 1, wherein the plurality of semipermeable hollow fiber membranes have an inner diameter of from about 2.8 mm to about 4.0 mm, and a wall thickness of from about 100 μm to about 500 μm, a ratio of the inner diameter to the wall thickness being larger than about 10.

7. The filtration device of claim 1, wherein the plurality of semipermeable hollow fiber membranes have a mean flow pore size, determined by capillary flow porometry, in a range of from about 0.2 μm to about 0.5 μm.

8. The filtration device of claim 1, wherein both the header section and the tubular section are welded to the disk by irradiation with laser light having a wavelength in a range of from about 800 nm to about 1090 nm.

9. The filtration device of claim 1, wherein the header section and the tubular section both comprise a material substantially transparent to IR light, and wherein the disk comprises from 0.1 to 10 wt.-% of the material substantially transparent to the IR light, relative to a total weight of the thermoplastic polymer.

10. A filtration device comprising:

a header section having an inlet for receiving an unfiltered liquid into the filtration device, a disk having a plurality of bores formed therein, the plurality of bores being defined by one or more walls within the disk, a plurality of semipermeable hollow fiber membranes, each semipermeable hollow fiber membrane having a first end and a second end, wherein the first end is welded to the one or more walls, wherein one or more semipermeable hollow fiber membranes is protruding from the disk, and wherein the second end is individually sealed by crimping; and a tubular section having an outlet for removing a filtered liquid from the filtration device;

wherein the header section covers a first face of the disk, wherein a lip of the header section contacts the disk and a lip of the tubular section contacts the disk, and wherein both the header section and the tubular section are welded to the disk; and wherein the tubular section covers a second face of the disk opposite the first face, and wherein the tubular section encloses the plurality of semipermeable hollow fiber membranes;

wherein the header section, the disk, and the tubular section each comprise a thermoplastic polymer; and wherein the disk comprises an infrared absorptive (IR-absorptive) pigment selected from the group consisting of carbon black, IR-absorptive inorganic pigments, and IR-absorptive organic pigments.

* * * * *